(12) United States Patent
Lilja et al.

(10) Patent No.: US 10,636,179 B2
(45) Date of Patent: Apr. 28, 2020

(54) PATIENT MOVEMENT CORRECTION METHOD FOR CONE-BEAM COMPUTED TOMOGRAPHY

(71) Applicant: PLANMECA OY, Helsinki (FI)

(72) Inventors: Mikko Lilja, Helsinki (FI); Kalle Karhu, Helsinki (FI); Jaakko Lahelma, Helsinki (FI); Kustaa Nyholm, Helsinki (FI); Ari Hietanen, Helsinki (FI); Timo Muller, Helsinki (FI); Sakari Kettunen, Helsinki (FI)

(73) Assignee: Planmeca OY, Helsinki (FI)

( * ) Notice: Subject to any disclaimer, the term of this patent is extended or adjusted under 35 U.S.C. 154(b) by 116 days.

(21) Appl. No.: 15/925,667

(22) Filed: Mar. 19, 2018

(65) Prior Publication Data

US 2018/0268574 A1    Sep. 20, 2018

(51) Int. Cl.
*G06T 11/00* (2006.01)
*A61B 6/03* (2006.01)
*A61B 6/00* (2006.01)
*G06T 7/00* (2017.01)

(52) U.S. Cl.
CPC .......... *G06T 11/008* (2013.01); *A61B 6/032* (2013.01); *A61B 6/4085* (2013.01); *A61B 6/466* (2013.01); *A61B 6/5264* (2013.01); *G06T 7/0012* (2013.01); *G06T 11/005* (2013.01); *G06T 11/006* (2013.01); *A61B 6/4441* (2013.01); *A61B 6/501* (2013.01); *G06T 2207/10081* (2013.01); *G06T 2207/10124* (2013.01); *G06T 2211/424* (2013.01)

(58) Field of Classification Search
CPC ... G06T 7/0012; G06T 11/003; G06T 11/005; G06T 11/008; G06T 2207/10081; A61B 6/4085; A61B 6/5264
See application file for complete search history.

(56) References Cited

U.S. PATENT DOCUMENTS

2016/0206272 A1 *   7/2016   Kyriakou .............. A61B 6/032
2017/0238897 A1 *   8/2017   Siewerdsen et al. .. A61B 6/025

* cited by examiner

*Primary Examiner* — Andrew W Johns
(74) *Attorney, Agent, or Firm* — Fay Sharpe LLP

(57) ABSTRACT

A patient movement correction method for cone-beam computed tomography wherein a set of X-ray projection images of the patient is acquired using the X-ray imaging means. An initial projection geometry estimate describing the spatial positions and orientation of the X-ray source and the X-ray detector during the acquisition of an X-ray projection images is defined. An intermediate CBCT reconstruction using the X-ray projection images and the initial projection geometry estimate is computed. Projection-image-specific corrective geometric transformations are determined for the initial projection geometry estimate and the intermediate CBCT reconstruction. A final CBCT reconstruction is computed using the X-ray projection images and a corrected estimate of the projection geometry corresponding to the determined corrective geometric transformations wherein the corrective geometric transformations for the initial projection geometry estimate are determined in a projection-image-specific rotating coordinate system corresponding to the spatial positions and orientations of the X-ray source and X-ray detector during the acquisition of the X-ray projection images.

13 Claims, 4 Drawing Sheets

PATIENT MOVEMENT CORRECTION METHOD FOR CONE-BEAM COMPUTED TOMOGRAPHY

FIELD OF INVENTION

The invention concerns patient movement correction methods in the field of cone-beam computed tomography.

BACKGROUND OF INVENTION

The following disclosure relates to three-dimensional X-ray cone-beam computed tomography for medical applications, wherein a plurality of X-ray projection images acquired from different angles are used to reconstruct 3-D cross-sectional images of an anatomy of a patient. The duration of the X-ray projection image acquisition is typically of the order of 10-30 seconds because the X-ray tube (X-ray source) and sensor (X-ray detector) must physically travel the spatial trajectory corresponding to the acquisition angles. The imaging trajectory is typically realized by a rotation and translation mechanism.

The imaging trajectory should be known with a sufficient accuracy and the imaged object should remain sufficiently stationary during the X-ray projection image acquisition in order for the reconstructed CBCT image to be sharp and true to the anatomy, because the projection image measurements are assumed to represent co-registered integrated views of a stationary object. This results in a set of geometrically consistent measurements that can be used to reconstruct the attenuation distribution representing the studied anatomy. Whenever these assumptions are violated, the accuracy of the reconstructed image is degraded as a consequence of the projection measurements becoming mutually inconsistent.

The accuracy of the final image typically depends on how accurately the assumptions made in the reconstruction process correspond to the actual, physical image acquisition process. The estimated spatial positions of the X-ray source and detector corresponding to each acquired X-ray image affect the computation of the ray paths during the CBCT reconstruction process. Due to inherent manufacturing and operating tolerances and potential deformation of the imaging device the realized rotation angles and positions tend to deviate from the ideal values according to the assumed form of the imaging trajectory. A systematic deviation, however, can be addressed by using different calibration methods that are repeated after certain period of time or operation cycles.

In medical CBCT imaging, the most significant source of geometric inaccuracy is the potential movement of the patient during the acquisition of the X-ray projection images. Namely, if the imaged object moves during the acquisition of the X-ray projection images, the effective spatial paths of the ray measurements become mutually inconsistent. Although it is well-known that the patient should not move and the patients are routinely instructed not to do so, a patient typically cannot remain completely stationary during the acquisition of the X-ray projections. This problem is typically addressed by supporting the patient. However, supporting the patient too tightly is inconvenient and uncomfortable. Furthermore, preventing all patient movement would require using a highly constraining support, which is not applicable in routine imaging.

In medical CBCT imaging both of the inaccuracies described above are present to some degree in all practical measurements. In a worst case scenario, the resulting geometric inconsistency of the projection image measurements may even require repeating the scan after a radiologist has inspected the quality of the image reconstruction. This is undesirable due to the radiation dose associated with the X-ray image acquisition, which is aimed to be kept as low as reasonably possible.

Computational approaches have been developed to address the problem of geometric inaccuracy in computed tomography imaging. In reported approaches in the literature, a virtual motion of the X-ray source and X-ray detector by means of a rigid geometric transformation in a fixed coordinate system has been applied to model and compensate for a rigid motion during the projection image acquisition. In recent approaches related to medical CBCT imaging, such geometric transformation is optimized by maximizing the sharpness of the resulting CBCT reconstruction. Typically such correction process is performed iteratively.

In CBCT imaging, applying a fixed coordinate system for the modelling and compensation of patient motion is not ideal, as the intrinsic geometric degrees-of-freedom in CBCT imaging are not separated by the coordinate system. In a CBCT imaging device, it is particular that the X-ray beams diverge and form a pyramid-shaped cone. As a result, a shift along the isoray adjoining the X-ray source and the center of the X-ray detector will only affect the magnification factor, whereas an in-plane shift along the X-ray detector's pixel array will result in a maximal shift of the imaged object within its projection image. Moreover, preventing a net transformation arising as a result of an applied geometric correction by known means of a rigid registration of the resulting corrected CBCT reconstruction and the uncorrected CBCT reconstruction is computationally expensive, especially if applied repeatedly during the geometric correction process.

BRIEF DESCRIPTION OF INVENTION

In the disclosed patient movement correction process for medical cone-beam computed tomography (CBCT), a data-driven algorithm utilizing an intrinsic, rotating coordinate system attached to the spatial positions and orientation of the X-ray source and detector is used to establish an improved estimate of the actual imaging geometry corresponding to the measured X-ray projection images. A net transformation in a fixed reference coordinate system is prevented by computing and subtracting the net transformation directly from the estimated corrective geometric transformation parameters. As a result, the relative positions of the X-ray source and detector system with respect to the patient, or vice versa, are retrospectively estimated and improved based on the X-ray projection image contents. The purpose of the correction process is to improve the resulting CBCT reconstruction image quality by improving the geometric consistency of the X-ray image measurements and, in turn, better to better satisfy the requirements of tomographic image reconstruction. The intrinsic coordinate system enables defining the applied geometric degrees-of-freedom in a manner that corresponds to their relative importance to both the correction process as well as the resulting image quality.

The disclosed patient movement correction process takes as its input the data that is normally required for computing a CBCT image reconstruction: a set of X-ray projection images and an estimate of the 3-D projection geometry corresponding to the spatial positions of the X-ray source and X-ray detector during the acquisition of the X-ray projection images. Similarly to corresponding methods, an intermediate reconstruction is first computed using the estimated projection geometry. Then, a corrective geometric transformation improving the geometric correspondence of each accessed X-ray projection image with the rest of the X-ray projection images is established with the transformation corresponding to a virtual movement of the X-ray source and detector during the image acquisition. In particular, a projection image-specific rotating coordinate system is applied for determining the corrective geometric transformation. The correction process, including the computation of an intermediate reconstruction using the current estimate of the projection geometry and the subsequent optimization of the corrective transformations, may be iterated for a number of times. After establishing the corrective geometric transformations, a final CBCT reconstruction is computed using the X-ray projection images and the final estimate of the projection geometry corresponding to the corrective transformations.

The benefit of the disclosed patient movement correction process before reconstructing the final CBCT image is an improvement in the projection geometric consistency, which results in a higher image quality in terms of sharpness, level of detail and contrast. A further benefit of the correction process is that by potentially preventing a re-scan due to projection geometry-related image quality degradation, the radiation dose incurred to the patient may be decreased.

BRIEF DESCRIPTION OF FIGURES

The accompanying drawings provide further understanding of the disclosed patient movement correction method. In the drawings.

DETAILED DESCRIPTION OF INVENTION

Figure 1:
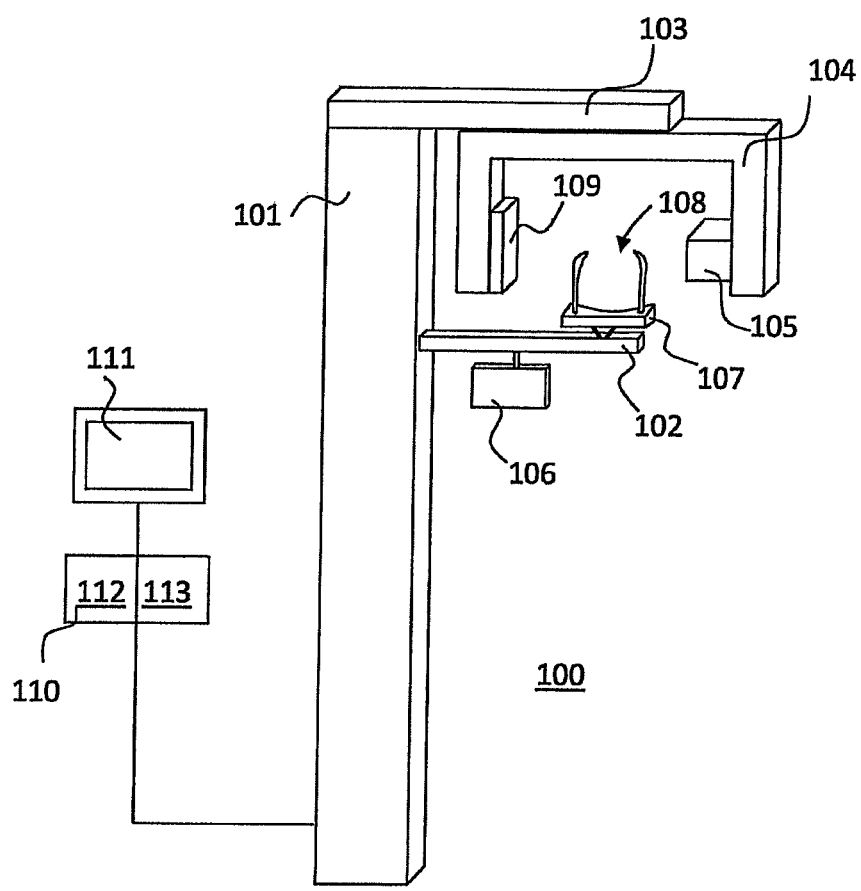
FIG. 1 shows an example of one typical CBCT imaging apparatus.

For computing a 3-D CBCT reconstruction, a number of 2-D X-ray projection images are measured using an X-ray source and X-ray detector that are rotated around the imaged anatomy. The exposure of each X-ray projection image takes typically in the range of milliseconds and when using typical scanning velocities, continuous movement of the X-ray source and detector does not any significant motion blurring in the projection images. In order to compute a 3-D reconstruction using a suitable method such as the FDK algorithm, the 3-D spatial positions of the X-ray source and detector in a suitable reference coordinate system comprising the imaging or projection geometry must be available to the reconstruction algorithm.

A typical description of the imaging geometry consists of the 3-D positions of the focus of the X-ray source and the center of the X-ray detector, and information to sufficiently uniquely determine the orientation of the X-ray detector. Such information may consist of e.g. rotation angles in a reference coordinate system that, when applied according to a predefined convention, will determine the directions of the horizontal and vertical axes of the detector's pixel array. The projection geometry description is typically based on knowledge of the imaging device's physical measures as well as the ideal exposure trajectories corresponding to given imaging program. Furthermore, a periodic calibration process is typically performed to ensure a sufficient accuracy of the projection geometry.

In the reconstruction process, the spatial propagation of X-radiation through the imaged anatomy is modeled. Typically, a rectilinear propagation is assumed for simplicity and the X-ray beam paths from the source to the detector are modeled as line integrals, which are computed based on the information contained in the projection geometry description. The spatial overlaps of the X-ray paths and the elements of the 3-D image voxel array used for the reconstruction are solved using a suitable projector algorithm and the projection geometry description. Based on the spatial overlaps and the measured values in the X-ray projection images, the total X-ray attenuation distribution corresponding to the imaged anatomy can be reconstructed using a suitable method such as the well-known FDK algorithm.

A fundamental assumption employed in the reconstruction process, however, is that the imaged anatomy has remained sufficiently stationary during the acquisition of the X-ray projection images. The rationale is that the X-ray projections should represent co-registered measurements of a stationary object that can then be consistently combined to reconstruct the 3-D structure of the object. A systematic error in the projection geometry can be compensated by a periodic calibration process, which eliminates the effects arising from any deviations from the assumed, ideal X-ray projection image acquisition trajectory.

A more difficult problem arises from patient movement during the imaging, which is unpredictable and random in its nature. Although it prevented to a degree by supporting the patient during the imaging, the relatively long duration of X-ray projection image acquisition in CBCT imaging, of the order of 10 seconds, makes it unfeasible to completely eliminate patient movement. Moreover, certain patients such as children and elderly find it more difficult to remain still during the imaging.

In the event of significant patient movement during the X-ray projection image acquisition, pronounced streak-like or blurring artefacts will ensue in the reconstructed image, which may in a worst case render the image useless for the intended medical purpose. Repeating the scan may provide a better result but at the cost of additional radiation dose.

In the disclosed retrospective approach for compensating the adverse effects of patient movement, an intermediate CBCT reconstruction is first computed using the 2-D X-ray projection images and the estimated imaging geometry. It is sufficient to compute the intermediate CBCT reconstruction at a coarser resolution than is typically used when making reconstructions for diagnostic purposes. The intermediate reconstruction serves to aggregate the information from all X-ray projection images with the appearance of the reconstruction reflecting the mutual geometric consistency of the measured 2-D X-ray projection images.

The optimization of the projection-image-specific geometry is based on measuring the similarity of the physical X-ray projection images and the corresponding re-projected data of the intermediate CBCT reconstruction that forms a digitally reconstructed radiograph (DRR). The rationale is that when the estimated projection geometry is consistent, the reconstructed image that by definition attempts to satisfy the measurements conveyed by the projection images in the sense of the forward projection operation will yield reprojections that will closely match the measured data. In the event of a geometric mismatch, the reprojection of the intermediate reconstruction will deviate from the measured projection. As the intermediate reconstruction serves as an aggregate of all projection images, its reprojection reflects the sum of all projection images and the maximum similarity of the measured X-ray projection image and the forward projected images can be expected to be maximized when the corresponding re-projection geometry matches the average correct projection geometry in the sense of the intermediate reconstruction.

In a typical CBCT imaging device, the emitted X-ray beams diverge and form a pyramid-shaped cone. A shift along the isoray adjoining the X-ray source and the center of the X-ray detector will only affect the magnification factor, whereas a shift along the X-ray detector plane will result in a maximal shift of the imaged object within its projection image. From this standpoint, the disclosed approach adopts a rotating coordinate system that is attached to the physical positions of the X-ray source and detector during the image acquisition. Namely, two of the coordinate axes are attached to the rectangular X-ray detector pixel array and the remaining perpendicular axis to the normal of the detector's pixel array. By limiting the geometric transformation of the projection geometry along these intrinsic axes for each projection image, it is possible to separate the geometric degrees-of-freedom, whose importance in the sense of the geometric accuracy varies.

When each X-ray projection image is subjected to an individual geometric transformation, it is possible that the resulting average transformation will incur a net effect on the reconstructed image. This manifests itself, e.g. as a global net shift or rotation of the reconstructed anatomy with respect to the uncorrected anatomy. It is possible that a net transformation of the anatomy will have adverse effects on the applicability of the reconstructed image. Thus, a compensation method for the net transformation is also disclosed. The net transformation can be estimated by mapping the transformation corresponding to each transformed projection image from the rotating coordinate system to the fixed coordinate system. For example, by assuming that each projection image is displaced only along its horizontal axis, the corresponding displacements in the fixed coordinate system can be computed based on the known horizontal axes of the projection-specific rotated coordinate systems, and the average value can be taken to represent the net displacement in the fixed coordinate system. By an inverse of the above-mentioned mapping, the inverse of the net transformation can be mapped back to the rotating coordinate systems and subtracted from the projection image-specific transformations. As a result, the net transformation in the fixed coordinate system is eliminated.

In the optimization process, the goodness of a corrective geometric transformation of a given X-ray projection image is measured by the similarity of the forward-projected image corresponding to the transformed projection geometry and the original X-ray projection image. The similarity of the reprojection and the X-ray projection can be measured e.g. by the mean squared difference of the images, correlation coefficient, or gradient correlation coefficient. The optimal (in the sense of the similarity measure) geometric transformation for each projection image given an intermediate CBCT reconstruction can then be determined by finding the extremum of the similarity measure between the forward-projected image and the X-ray projection image as a function of the parameters of the geometric transformation.

The optimization process then includes computing an intermediate CBCT reconstruction using the initial estimate of the X-ray projection geometry; accessing all or a subset of the measured X-ray projection images; (for each accessed projection image) establishing a projection image-specific corrective transformation by finding the maximum similarity between the measured X-ray projection image and the corresponding forward projection of the intermediate CBCT reconstruction as a function of the parameters of the geometric transformation performed in the rotating coordinate system; estimating the net transformation in a fixed reference coordinate system and subtracting the corresponding transformation from the transformation parameters in the rotating coordinate system; computing a final CBCT reconstruction when a sufficient correction result is estimated to have been obtained.

In FIG. 1, an example of a medical CBCT imaging apparatus 100 is shown with which includes a vertical base construction 101 from which horizontally extends a support structure 102, a patient support means 107 and an arm part 103 which supports a structure supporting the imaging means, an arm part 104. To the arm part supporting the imaging means 104 there are arranged at a distance from each other an X-ray source 105 and a receiver means of X-ray image information (X-ray detector) 109 that are arranged with respect to the patient support means 107 such that an imaging station 108 positioned between the X-ray source 105 and the receiver means of X-ray image information 109 is formed such that a beam generated by the X-ray source 105 is alignable to go through the imaging station 108 towards the receiver means of X-ray image information 109. The arm part 104 supporting the imaging means is arranged to be rotatable, and also its location with respect to the structure supporting it 103 and/or the patient support station 108 may be arranged changeable. The arrangement includes a control means, of which FIG. 1 shows a control panel 106 placed in connection with the support structure 102 supporting the patient support means 107. The imaging apparatus 100 can be arranged to be connected to a controller 110 via a cable, the controller including a computer arranged with a means for processing image information produced by the imaging apparatus, and a display 111 on which images can be shown. The controller 110 further comprises at least one processor 112 and at least one memory 113. The at least one processor 112 may be configured to execute computer programs and the at least one memory 113 is configured to store computer programs and related data. The controller 110 may be or include a general purpose computer or a specifically manufactured device for implementing the process described below.

Figure 2:
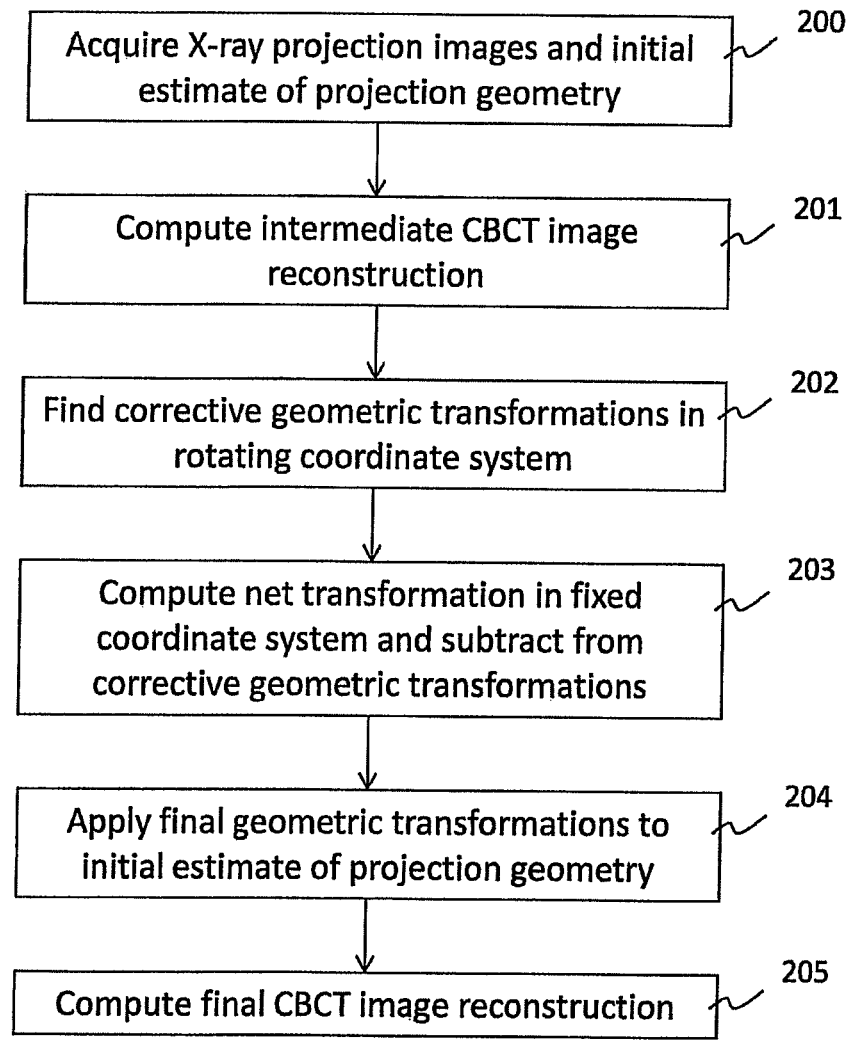
FIG. 2 shows a flow chart of the disclosed patient movement correction method.

FIG. 2 describes the steps of the disclosed patient movement correction method that may be used, for example, for processing images acquire by the imaging arrangement of FIG. 1. The method is based on finding corrective geometric transformations for the initially estimated projection geometry in a rotating coordinate system attached to the positions of the X-ray source 105 and X-ray detector 109.

In step 200 of the method of FIG. 2, the input data is acquired comprising the measured X-ray projection images and an initial estimate of the projection geometry corresponding to the acquisition process. In the arrangement of FIG. 1, the projection geometry defines the physical trajectory of the X-ray source 105 and X-ray detector 109 when they are rotated and translated around the imaging station 108 by means of the arms 103 and 104. The projection geometry also determines the estimated orientation of the X-ray detector 109. The form of the projection geometry is typically based on a geometry calibration procedure utilizing e.g. a known reference phantom with radiopaque markers.

In step 201, an intermediate CBCT reconstruction for the purpose of the projection optimization method is computed using the input data acquired in step 200. It is possible to use downsampled versions of the input data, as it is typically not necessary to apply as high spatial resolution as in the CBCT images intended for diagnostic purposes. The intermediate reconstruction is understood to aggregate all available physical and geometric information acquired during the measurement process in step 200. In the event of geometric inconsistency, this is reflected by the intermediate reconstruction by e.g. blurriness of the reconstructed details.

In step 202, corrective geometric transformations for the projection images are established in the rotating coordinate system. The purpose of the geometric transformations is to compensate for the intrinsic geometric inconsistency, in the initial estimate of the projection geometry. The details of step 202 are explained below in reference to FIG. 3 but, more generally, the corrective geometric transformation is sought by finding the optimal geometric transformation. The goodness of a transformation is defined by assigning a similarity value to it. The similarity value is computed by comparing a reprojected digitally reconstructed radiograph (DRR) of the intermediate CBCT image reconstruction to the corresponding measured X-ray projection image, with the applied projection geometry corresponding to the evaluated geometric transformation. A higher similarity value is taken as an indication of a better corrective geometric transformation. Applying the rotating coordinate system for the geometric transformation enables separating the geometric degrees-of-freedom according to their significance to the problem in a cone-beam projection geometry.

In step 203, the net geometric transformation in a fixed coordinate system is subtracted. The fixed coordinate system is defined typically in reference to static components of the imaging apparatus 100, such as components of the imaging apparatus fixed in connection with the imaging station 108. The net geometric transformation is computed by linearly transforming the geometric transformations established in step 202 from the rotating coordinate system to the fixed coordinate system. The linear transformation is readily obtained based on the known coordinate axes of the rotated and fixed coordinate systems. After the net transformation has been established, its inverse is linearly transformed from the fixed coordinate system to its rotated coordinate system. The inverse of the net transformation then corresponds to a set of geometric transformation parameters for each projection image in the rotating coordinate system. Adding these values to the geometric parameter values established in step 202 will result in the net transformation being canceled out in the fixed coordinate system.

In step 204, the transformation parameter values resulting from step 203 are applied to the initial projection geometry estimate to obtain the corrected projection geometry estimate. In particular, steps 201-203 may be repeated iteratively a plurality of times before advancing to step 204.

In step 205, the final CBCT reconstruction is computed using the corrected projection geometry estimate. The final CBCT reconstruction is computed in a normal manner with the exception to the situation where steps 201-204 were not applied that the initial projection geometry estimate is replaced by the corrected projection geometry estimate obtained in steps 201-204.

Figure 3:
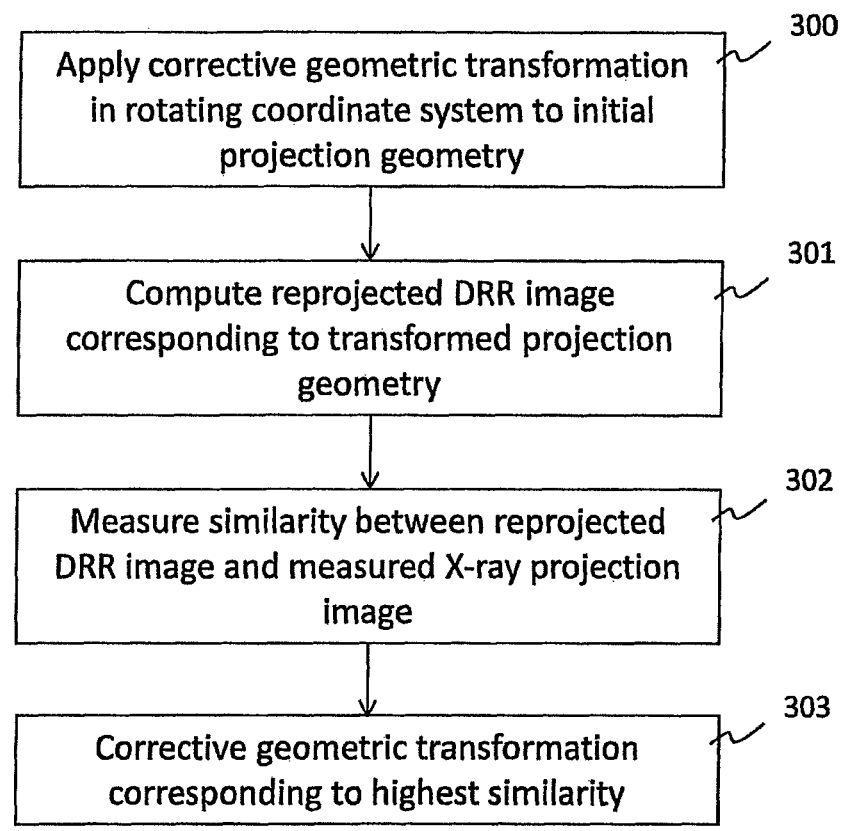
FIG. 3 shows a flow chart detailing the step 203 of FIG. 2.

FIG. 3 describes as an example details of step 202 according to FIG. 2. In step 300, the assessed geometric transformation is applied to the initial geometry of a projection image in the rotating coordinate system. Again, the coordinate system is defined to coincide with the spatial positions and orientation of the X-ray source 105 and X-ray detector 109 during the physical acquisition of the considered projection image. Applying the transformation in the rotating frame of reference involves a linear mapping from the fixed coordinate system, where the imaging geometry is typically defined, to the rotating coordinate system, where the transformation is performed, followed by an inverse linear mapping from the rotating coordinate system to the fixed coordinate system. As a simple example of the accomplished effect, for applying a translation along the horizontal axis of the X-ray detector 109, the initial projection geometry of the projection image is mapped to the rotating coordinate system, translated along this axis of the rotating coordinate system by the given amount, which corresponds to a virtual movement of the X-ray source and detector, and then mapped back to the fixed coordinate system. The transformed projection geometry is expressed in the fixed coordinate system and the obtained transformed projection geometry is used as input for the subsequent step 301.

In step 301, a reprojected DRR image of the intermediate CBCT reconstruction computed in step 201 is computed using the transformed projection geometry obtained in step 300. The computation of the DRR image can be performed using a standard algorithm such as the Siddon raycasting method. In a typical reprojection algorithm, the input of the algorithm consists of the end points of the 3-D X-ray representation and the source image of which the DRR image is computed including knowledge of its spatial position and orientation expressed in the same coordinate system. In the described setting, this coordinate system corresponds to the fixed coordinate system. The effect of the geometric transformation applied in step 300 is to change the end points of each virtual X-ray path through the intermediate CBCT reconstruction, which propagates the effect of the geometric transformation to the obtained DRR image.

In step 302, the similarity between the DRR image obtained in step 301 and the X-ray projection image acquired in step 200 is evaluated. The similarity is based on a pointwise comparison of the images using established approaches such as the average squared difference of the images or their cross-correlation. The specific measure used for evaluating the similarity is not significant to the described method. The obtained similarity value is assigned to the geometric parameters given as input to step 300. A higher similarity is taken as an indication of more suitable geometric transformation parameters.

In step 303, the optimal geometric transformation parameters are established by finding the parameters corresponding to the highest similarity value obtained by applying steps 300-302. In a typical setting, steps 300-302 are repeatedly evaluated by a suitable minimization algorithm such as the well-known Nelder-Mead simplex algorithm to establish the optimal geometric transformation parameters. These parameters are stored and assigned to the specific projection image until they are potentially changed by a repetition of steps 201-203.

Figure 4:
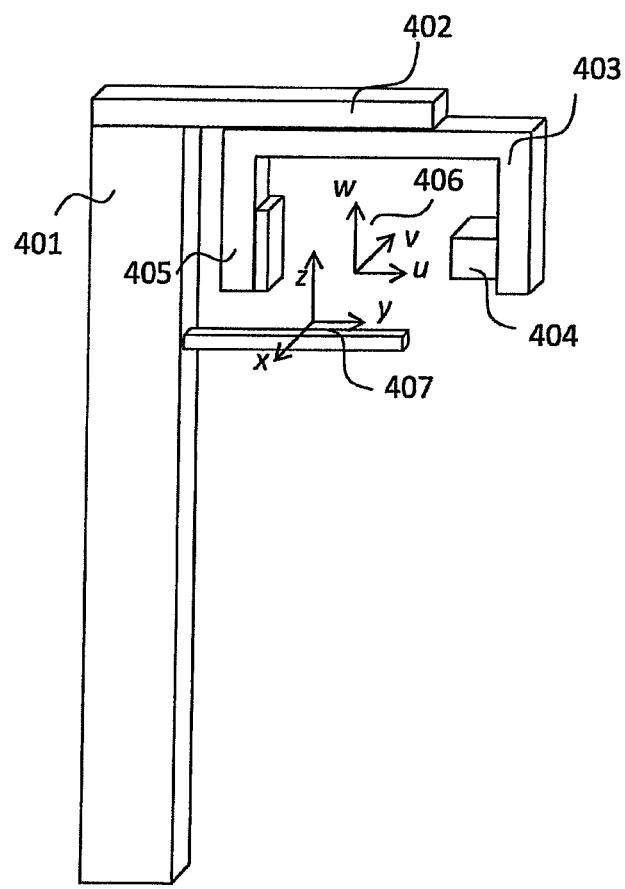
FIG. 4 shows in the context of a CBCT imaging apparatus a rotating coordinate system applied in the disclosed patient movement correction method.

FIG. 4 illustrates the rotating coordinate system applied in step 202. In a CBCT imaging apparatus, a C-arm part 403 typically supports the X-ray source 404 and X-ray detector 405. The C-arm is supported by the vertical base construction 401 and a shoulder arm part 402. In CBCT imaging, it is particular that the X-ray beams diverge and form a pyramid-shaped cone. A shift along the isoray adjoining the X-ray source 404 and the center of the X-ray detector 405 will only affect the magnification factor, whereas a shift in the plane of the X-ray detector's pixel array will result in a maximal shift of the imaged object within its projection image. From this standpoint, the disclosed approach adopts a rotating uvw coordinate system 406 that is attached to the physical positions and orientations of the X-ray source and detector pixel array during the image acquisition. By limiting the geometric transformation of the projection geometry along these intrinsic axes for each projection image, it is possible to separate the geometric degrees-of-freedom, whose importance in the sense of the geometric accuracy varies. The fixed coordinate system, where the net transformation is computed is denoted by the xyz coordinate system 407.

Setting the u axis of the coordinate system to coincide with the normal of the X-ray detector and the v axis with the horizontal axis of the X-ray detector's pixel array, these degrees-of-freedom are, for example, for a rigid transformation:

1. Longitudinal shift along the normal of the X-ray detector's pixel array (u axis); 2. Lateral shift along the horizontal axis of the X-ray detector's pixel array (v axis); 3. Vertical shift along the vertical axis of the X-ray detector's pixel array (w axis); 4. Rotation around the u axis (roll angle); 5. Rotation around the v axis (pitch angle); 6. Rotation around the w axis (yaw angle).

The result of the disclosed patient movement correction method is an improved estimate of the projection geometry corresponding to the physical acquisition of the X-ray projection images and correspondingly a CBCT reconstruction image, where the effect of geometric inconsistency has been reduced.

The disclosed method may be implemented as computer software executed in a computing device. The software is embodied on a computer readable medium so that it can be provided to the computing device, such as the controller 110 of FIG. 1.

As stated above, the components of the exemplary embodiments can include computer readable medium or memories for holding instructions programmed according to the teachings of the present embodiments and for holding data structures, tables, records, and/or other data described herein. Computer readable medium can include any suitable medium that participates in providing instructions to a processor for execution. Common forms of computer-readable media can include, for example, a floppy disk, a flexible disk, hard disk, magnetic tape, any other suitable magnetic medium, a CD-ROM, CD+R, CD+RW, DVD, DVD-RAM, DVD+RW, DVD+R, HD DVD, HD DVD-R, HD DVD-RW, HD DVD-RAM, Blu-ray Disc, any other suitable optical medium, a RAM, a PROM, an EPROM, a FLASH-EPROM, any other suitable memory chip or cartridge, a carrier wave or any other suitable medium from which a computer can read.

It is obvious to a person skilled in the art that with the advancement of technology, the basic idea of the self-calibrating medical imaging apparatus may be implemented in various ways. The self-calibrating medical imaging apparatus and its embodiments are thus not limited to the examples described above; instead they may vary within the scope of the claims.

The invention claimed is:

1. A patient movement correction method for cone-beam computed tomography comprising:
   acquiring a set of X-ray projection images of the imaged patient using an X-ray imaging means containing an X-ray source and X-ray detector;
   defining an initial projection geometry estimate describing the spatial positions and orientation of the X-ray source and the X-ray detector during the acquisition of the X-ray projection images;
   computing an intermediate CBCT reconstruction using the X-ray projection images and the initial projection geometry estimate;
   determining projection-image-specific corrective geometric transformations for the initial projection geometry estimate based on the X-ray projection images, the initial projection geometry estimate, and the intermediate CBCT reconstruction;
   and computing a final CBCT reconstruction using the X-ray projection images and a corrected estimate of the projection geometry corresponding to the determined corrective geometric transformations
   characterized in that the corrective geometric transformations for the initial projection geometry estimate are determined in a projection-image-specific rotating coordinate system corresponding to the spatial positions and orientations of the X-ray source and X-ray detector during the acquisition of the X-ray projection images.

2. A method according to claim 1, wherein said projection-image-specific rotating coordinate system is defined by setting two perpendicular axes to coincide with the X-ray detector's pixel array and third perpendicular axis to coincide with the normal of the X-ray detector's pixel array.

3. A method according to claim 2, further comprising determining the projection-image-specific corrective geometric transformation for the initial projection geometry estimate based on a re-projected digitally reconstructed radiograph obtained by applying a geometric transformation in the rotating coordinate system to the initial projection geometry estimate.

4. A method according to claim 3, wherein the corrective geometric transformations are determined by finding the maximal similarity between the X-ray projection images and corresponding re-projected digitally reconstructed radiographs of the intermediate CBCT reconstruction.

5. A method according to claim 4, wherein a net transformation in a fixed coordinate system is computed and subtracted from the corrective geometric transformations determined in the rotating coordinate system.

6. A method according to claim 5, wherein the net transformation in the fixed coordinate system is computed by mapping the projection-image-specific geometric transformations from the rotating coordinate system to the fixed coordinate system and taking their average, and the average subtracted from the geometric transformations after a mapping from the fixed coordinate system to the rotating coordinate system.

7. A method according to claim 6, wherein the computation of the intermediate CBCT reconstruction and determining the corrective geometric transformations are iterated a plurality of times, with the corrected projection geometry estimate after each iteration acting as a new initial projection geometry estimate for the following iteration, and the final corrected projection geometry estimate corresponding to the corrected projection geometry estimate of the last applied iteration.

8. A method according to claim 1, further comprising determining the projection-image-specific corrective geometric transformation for the initial projection estimate based on a re-projected digitally reconstructed radiograph obtained by applying a geometric transformation in the rotating coordinate system to the initial projection geometry estimate.

9. A method according to claim 1, wherein the corrective geometric transformations are determined by finding the maximal similarity between the X-ray projection images and corresponding re-projected digitally reconstructed radiographs of the intermediate CBCT reconstruction.

10. A method according to claim 1, wherein a net transformation in a fixed coordinate system is computed and subtracted from the corrective geometric transformations determined in the rotating coordinate system.

11. A method according to claim 1, wherein the net transformation in the fixed coordinate system is computed by mapping the projection-image-specific geometric transformations from the rotating coordinate system to the fixed coordinate system and taking their average, and the average subtracted from the geometric transformations after a mapping from the fixed coordinate system to the rotating coordinate system.

12. A method according to claim 1, wherein the computation of the intermediate CBCT reconstruction and determining the corrective geometric transformations are iterated a plurality of times, with the corrected projection geometry estimate after each iteration acting as a new initial projection geometry estimate for the following iteration, and the final corrected projection geometry estimate corresponding to the corrected projection geometry estimate of the last applied iteration.

13. An apparatus comprising:
- at least one processor configured to execute computer programs; and
- at least one memory configured to store computer programs and the related data; characterized in that the apparatus is connectable to a medical imaging apparatus and configured to perform a method according to claim 1.

* * * * *